United States Patent
Yasuda et al.

(10) Patent No.: US 6,313,477 B1
(45) Date of Patent: Nov. 6, 2001

(54) METHOD OF AND APPARATUS FOR READING RADIATION IMAGES AND CORRECTING SHADING AND/OR FADING OF THE IMAGES

(75) Inventors: Hiroaki Yasuda; Naoto Iwakiri, both of Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/280,843

(22) Filed: Mar. 30, 1999

(30) Foreign Application Priority Data

Mar. 30, 1998 (JP) .................................................. 10-083672

(51) Int. Cl.⁷ .................................................... G01N 23/04
(52) U.S. Cl. ........................... 250/587; 250/584; 250/586
(58) Field of Search .................................... 250/584, 586, 250/587

(56) References Cited

U.S. PATENT DOCUMENTS

| | | | |
|---|---|---|---|
| 4,258,264 | 3/1981 | Kotera et al. | 250/585 |
| 4,346,295 | 8/1982 | Tanaka et al. | 250/586 |
| 4,485,302 | 11/1984 | Tanaka et al. | 250/585 |
| 4,734,783 | 3/1988 | Horikawa | 358/448 |
| 4,860,116 * | 8/1989 | Nakajima | 358/447 |
| 4,885,467 * | 12/1989 | Horikawa | 250/587 |
| 4,922,100 * | 5/1990 | Takeuchi | 250/584 |
| 4,985,629 | 1/1991 | Horikawa | 250/585 |
| 5,028,783 * | 7/1991 | Arakawa | 250/587 |
| 5,051,588 * | 9/1991 | Agano | 250/587 |
| 5,086,228 * | 2/1992 | Kojima | 250/587 |
| 5,266,804 * | 11/1993 | Shimizu | 250/584 |
| 5,477,059 * | 12/1995 | Arakawa | 250/587 |
| 5,483,081 * | 1/1996 | Hosoi | 250/585 |
| 5,550,385 * | 8/1996 | Nanami et al. | 250/584 |
| 5,602,402 * | 2/1997 | Yasuda | 250/587 |
| 5,654,556 * | 8/1997 | Yasuda | 250/584 |
| 5,832,055 * | 11/1998 | Dewaele | 378/62 |
| 5,877,508 * | 3/1999 | Arakawa et al. | 250/588 |
| 5,969,652 * | 10/1999 | Iwakiri | 341/118 |
| 6,239,448 * | 5/2001 | Kawai | 250/586 |

FOREIGN PATENT DOCUMENTS

| | | | |
|---|---|---|---|
| 56-11395 | 2/1981 | (JP) | G21K/4/00 |
| 59-72079 | 4/1984 | (JP) | G01T/1/29 |
| 61-189763 | 8/1986 | (JP) | H04N/1/04 |
| 63-165842 | 7/1988 | (JP) | G03B/42/02 |
| 64-86759 | 3/1989 | (JP) | H04N/1/04 |
| 4-157440 | 5/1992 | (JP) | G03B/42/02 |

* cited by examiner

Primary Examiner—Robert H. Kim
Assistant Examiner—Allen C. Ho
(74) Attorney, Agent, or Firm—Sughrue, Mion, Zinn Macpeak & Seas, PLLC

(57) ABSTRACT

In a two-side radiation image reading method wherein a stimulable phosphor sheet storing a radiation image is scanned by stimulating rays and light emitted from the front and back sides of the sheet is photoelectrically detected by photoelectric reading means separately located on the front and back sides of the sheet to obtain two image signals representing the radiation image to be subjected to addition processing or the like for obtaining a final image, shading correction data and/or fading correction data are obtained in advance and shading correction and/or fading correction is carried out on the image signals by using the correction data having been obtained. While an area equivalent to one side of the stimulable phosphor sheet (whose number of main scan lines is 4320) is being scanned, reading of the sheet is switched between the front and back sides and sensitivity of photoelectric reading means is also changed (to standard, semi-high, and high).

21 Claims, 10 Drawing Sheets

METHOD OF AND APPARATUS FOR READING RADIATION IMAGES AND CORRECTING SHADING AND/OR FADING OF THE IMAGES

BACKGROUND OF THE INVENTION

The present invention relates to an improvement in a method of acquiring shading and/or fading correction data for a radiation image reading apparatus which reads image signals from both sides of a stimulable phosphor sheet storing a radiation image.

Description of the Related Art

Radiation image recording reproducing systems using stimulable phosphor which emits light, upon exposure to a stimulating ray such as visible light, in accordance with radiation energy stored therein originated form radioactive rays (such as X rays, α rays, β rays, γ rays, electron rays, and ultraviolet rays) have been irradiated thereon have been known (see Japanese Unexamined Patent Publication Nos. 55(1980)-12429, 56(1981)-11395, and 56(1981)-11397, for example). A radiation image recording reproducing system records radiation image information of a subject such as a human body on a stimulable phosphor sheet and causes the sheet to emit light by scanning the sheet with a laser beam or the like. The emitted light is read photoelectrically and an image signal is thereby obtained. Based on the image signal, the radiation image recording reproducing system causes the radiation image of the subject to be output as a visual image on a recording medium such as a photosensitive material or on a radiation image display apparatus. A system of this kind is practically advantageous in terms of capability of recording an image in an extremely wide radiation exposure range compared to radiography systems using conventional silver halide film photographs.

However, in some cases, image information reading apparatuses used in the radiation image recording reproducing systems described above have fluctuations of image signals obtained by their photoelectric reading means, caused by unevenness in strength of a scanning beam due to a fluctuation in reflectance of a reflection plane of a photodeflector (such as a polygon mirror) for scanning with stimulating rays, or caused by a scanning speed fluctuation due to variance of deflection speed of the photodeflector, or caused by uneven delectability due to variance in sensitivity along the main scan direction of photoelectric reading means such as a photomultiplier (photomultiplier tube) having an elongated shape and placed along the main scan direction. Once a partial reduction (shading) in photodetection efficiency due to such unevenness occurs, it becomes impossible to properly detect image information recorded on the scanned surface.

The applicant has already proposed a shading correction method and the like (see Japanese Unexamined Patent Publication Nos. 61(1986)-189763, 62(1987)-47259, 62(1987)-47261, 64(1989)-86759, and 2 (1990)-58973, for example) which avoidthe effects of shading by correcting image signals or the sensitivity of photoelectric reading means corresponding to main scan position of a beam, for example, based on a shading characteristic (shading correction data) pre-detected by using a stimulable phosphon sheet on which radioactive rays have been irradiated uniformly.

Furthermore, the stimulable phosphor sheets used in such radiation image recording reproducing systems have a phenomenon (fading phenomenon) such that the amount of light emitted therefrom decreases when the stimulable phosphor sheets are stimulated by stimulating rays, due to gradual loss in the radiation energy stored thereon, in accordance with time elapsed after recording of a radiation image on a stimulable phosphor sheet, and progresses with time elapsed thereafter. In the system described above, the phenomenon causes lower sensitivity of the image signal read by the system, in the case where there is a time-lag between radiation image recording and image signal reading by exposure of the sheet to the stimulating ray. Furthermore, in a system carrying out pre-reading, a main reading condition determined by pre-reading becomes inappropriate due to the fading phenomenon if there is a time-lag between pre-reading and main reading.

It has been known that the loss of radiation energy stored on a stimulable phosphor sheet reaches an equilibrium state after a certain amount of time has elapsed after irradiating radiation on the sheet. Therefore, after the certain amount of time has elapsed, no fluctuation with time due to the fading effect is observed when the image signal representing a radiation image is obtained from the stimulable phosphor sheet. Consequently, if image signals are obtained upon exposure of the stimulable phosphor sheets to a stimulating ray after fluctuation with time due to the fading effect has been diminished, no fluctuation in image signal levels due to the elapsed time is observed and images having temporarily uniform quality can be obtained. However, since some amount of time is necessary for the fading phenomenon to reach the equilibrium state, efficient reading has not been carried out in the case where images have temporarily uniform quality are sought.

In order to efficiently obtain images having temporally uniform quality by promoting radiation energy loss caused by fading, a radiation image reading method wherein a stimulable phosphor sheet is heated to promote radiation energy loss due to fading, before exposure to a stimulating ray and after irradiation of a radioactive ray thereon, so that radiation energy loss from the sheet after the radioactive ray has been irradiated thereon can promptly reach the equilibrium state has been proposed (Japanese Unexamined Patent Publication No. 59(1984)-72079).

Furthermore, another radiation image reading method wherein a stimulable phosphor sheet storing a radiation image is chilled immediately after radiation has been irradiated thereon so that loss of the radiation energy stored on the sheet is prevented and image reproducibility is improved by suppressing the fading effect, has also been proposed (Japanese Unexamined Patent Publication No. 63(1988)-165842).

Moreover, taking fading into consideration, a main reading condition correcting method wherein a main reading condition temporarily determined through pre-reading is correted so that an appropriate reading condition is always output has been proposed (Japanese Unexamined Patent Publication No. 4(1992)-157440). In this method, a fading characteristic in accordance with time elapsed after photographing is pre-stored. The amount of fading at pre-reading is thus found by measuring the time elapsed from photographing to pre-reading and the amount of fading at main reading is also found by measuring the time elapsed from photographing to mainreading. The sensitivity at mainreading temporarily set based on a pre-read signal is corrected based on the fading amount difference between pre-reading and main reading. In other words, a fading characteristic in accordance with time Elapsed after photographing is pre-stored, and the amount of fading at pre-reading (F1) is found from time (T1) elapsed between photographing and pre-reading. The amount of fading at main reading (F2) is also found from time (T2) elapsed between photographing and reading. The sensitivity (Sk) temporarily set based on a signal at pre-reading is then corrected based on the fading amount difference (F1–F2) between pre-reading and main reading.

Meanwhile, as a method of photoelectrically reading the emitted light, a radiation image reading apparatus which comprises photoelectric reading means separately located on the front and back sides of a stimulable phosphor sheet and respectively reads the light emitted from both sides of the sheet by using the photoelectric reading means on both sides while irradiating a stimulating ray either on one side or on both sides to scan the sheet, has been proposed (see Japanese Unexamined Patent Publication No. 55(1980)-87970, for example). Such a radiation image reading apparatus has an improved light collection efficiency and thus an improved S/N ratio, since one stimulable phosphor sheet has recorded one radiation image and the light emitted therefrom can be collected by the photoelectric reading means on both sides of the sheet.

When shading correction or fading correction is carried out by the radiation image reading apparatus reading light from both sides of a sheet, the image signal acquired from either side of the sheet has a shading/fading characteristic different from that of the other side, and it is necessary to carry out respective correction for each side.

It is, therefore, necessary to obtain correction data for each side of the sheet, which doubles the time necessary for only one side. It is possible to acquire shading correction data simultaneously for both sides, but this is not practical, since systems for obtaining the shading correction data are necessary for both sides.

The present invention has been created based on consideration of the above problems. An object of the present invention is to provide a method of promptly and easily acquiring shading/fading correction data for a radiation image reading apparatus which carries out two-side reading.

Another object of the present invention is to provide a radiation image reading method and apparatus for promptly and easily correcting shading/fading by using the shading/fading correction data obtained by the radiation image reading apparatus carrying out two-side reading.

SUMMARY OF THE INVENTION

A radiation image reading method of the present invention is a two-side radiation image reading method comprising the steps of scanning a stimulable phosphor sheet storing a radiation image by using stimulating rays, photoelectrically detecting light emitted from the front and back sides of the sheet by using photoelectric reading means separately located on both sides of the sheet to read 2 image signals representing the radiation image, and obtaining a final image by carrying out addition processing or the like on the 2 image signals, and further includes the steps of acquiring shading correction data and/or fading correction data in advance and carrying out shading correction and/or fading correction on the image signals by using the shading correction data and/or fading correction data.

The correction may be carried out by applying shading correction data and/or fading correction data corresponding to the image after addition processing to images of only the front side or the back side of stimulable phosphor sheets so that uniformity of the images after addition can be obtained. Alternatively, the above correction may be carried out on images of both sides of a stimulable phosphor sheet so that each image is subjected to the same correction. Furthermore, the correction may be carried out on images after addition by using shading correction data and/or fading correction data corresponding to the image after addition processing.

A radiation image reading apparatus of the present invention is a two-side radiation image reading apparatus which scans, by using stimulating rays, a stimulable phosphor sheet on which a radiation image has been recorded, photoelectrically detects the light emitted from the front and back sides of the sheet by using photoelectric reading means separately located on both sides of the sheet to read 2 image signals representing the radiation image, obtains a final image by carrying out additional processing or the like on the 2 image signals, and the radiation image reading apparatus further comprises correction means for carrying out shading correction and/or fading correction on the image signals by suing shading correction and/or fading correction data obtained in advance.

The correction means may carry out the correction by applying shading correction data and/or fading correction data corresponding to the image after addition processing to images of only the front side or the back side of stimulable phosphor sheets so that uniformity of the images after addition can be retained. Alternatively, the above correction may be cared out on images of both sides of a stimulable phosphor sheet so that each image is subjected to the same correction. Furthermore, the correction may be carried out on images after addition by using the shading correction data and/or fading correction data corresponding to the image after addition processing.

Another shading correction data and/or fading correction data acquiring method of the present invention is for a two-sided radiation image reading apparatus which scans, by using stimulating rays, a stimulable phosphor sheet on which a radiation image has been recorded and photoelectrically detects light emitted from the front and back sides of the sheet by using photoelectric reading means separately located on both sides of the sheet to read 2 image signals representing the radiation image, and the shading correction data and/or fading correction data acquiring method acquires shading correction data and/or fading correction data corresponding to the front and back sides of a stimulable phosphor sheet at one-time reading.

In this case, the shading correction data and/or fading correction data may be recorded in image memories corresponding to both sides or in memories which are separated from the image memories and are for shading and/or fading correction data acquisition corresponding to both sides.

Alternatively, in the shading correction data and/or fading correction data acquiring method for the above two-side radiation image reading apparatus, the shading correction data and/or fading correction data corresponding to both sides may be acquired by two-time reading, one of which is for the front side and the other for the back side.

In this case, the shading correction data and/or fading correction data may be recorded in an image memory corresponding to only any one of the front side image, the back side image, and a post-addition image, or in a memory which is separated from the image memory and is for acquisition of the shading correction data and/or fading correction data corresponding to only any one of the front side image, the back side image and a post-addition image.

Still another correction data acquiring method of the present invention is characterized by the fact that shading correction data and/or fading correction data are obtained through calculation using an image after addition processing.

In such a shading correction data and/or fading correction data acquiring method, a plurality of shading correction data and/or fading correction data sets in accordance with reading modes such as scanning density of stimulating rays, a beam diameter of the scanning stimulating rays, and a scanning speed, can be obtained.

Among the sets of shading correction data and/or fading correction data in accordance with reading modes such as scanning density of a stimulating ray, a beam diameter of the scanning stimulating ray, and a scanning speed, a set of shading correction data and/or fading correction data corresponding to an actual reading mode may be used for shading correction and/or fading correction on the image signal.

The above-method is applicable to not only the two-side reading but also one-side reading. In other words, in a radiation image reading method wherein a stimulable phosphor sheet on which a radiation image has been recorded is scanned by stimulating rays and light emitted from the sheet is photoelectrically detected by photoelectric reading means for reading an image signal representing the image, the present invention is characterized by the fact that a plurality of shading correction and/or fading correction data sets are obtained in accordance with reading modes such as a scanning density of the stimulating rays, a beam diameter of the scanning stimulating rays, and a scanning speed.

Likewise, in a radiation image reading method wherein a stimulable phosphor sheet on which a radiation image has been recorded is scanned by stimulating rays and light emitted from the sheet is photoelectrically detected by the photoelectric reading means for reading an image signal representing the image, the present invention is characterized by the fact that a plurality of shading correction and/or fading correction data sets are obtained in advance in accordance with reading modes such as a scanning density of the stimulating rays, a beam diameter of the scanning stimulating rays, and a scanning speed, and shading correction and/or fading correction is carried out at an actual reading on the image signal by using a shading correction and/or fading correction data set corresponding to the actual reading mode among the sets of shading correction data and/or fading correction data having been obtained.

In a radiation image reading apparatus which scans, by using a stimulating ray, a stimulable phosphor sheet on which a radiation image has been recorded and photoelectrically detects the light emitted from the front and back sides of the sheet by using photoelectric reading means separately located on both sides of the sheet to read two image signals representing the radiation image, yet another shading and/or fading correction data acquiring method of the present invention acquires shading/fading correction data by scanning a stimulable phosphor sheet whereon radioactive rays have been irradiated uniformly, and is characterized by the fact that the shading and/or fading correction data for both sides of the sheet are obtained by switching reading between the two photoelectric reading means while the stimulable phosphor sheet is being scanned with the stimulating rays.

Switching reading by the photoelectric reading means between one side and the other side may be carried out based on the number of main scan lines having been scanned by the stimulating rays or based on time elapsed after detection of a reference signal marking the start of image signal reading.

Moreover, sensitivity of each photoelectric reading means can be switched so that the shading and/or fading correction data for different sensitivity levels can be obtained for each photoelectric reading means. Switching reading by the photoelectric reading means between one side and the other side may be carried out based on the number of main scan lines having been scanned by the stimulating rays or based on the time elapsed after detection of a reference signal marking the start of image signal reading.

A shading and/or fading correction data acquiring method for the radiation image reading apparatus of the present invention obtains shading and/or fading correction data for the front and back sides of a stimulable phosphor sheet while an area equivalent to one side of the stimulable phosphor sheet whereon radiation has been irradiated uniformly is being scanned with stimulating rays, by switching reading between the front and back sides by suing photoelectric reading means located on both sides.

In other words, in a radiation image reading apparatus which scans, by using stimulating rays, a stimulable phosphor sheet on which a radiation image has been recorded and photoelectrically detects light emitted from the front and back sides of the sheet by using photoelectric reading means separately located on both sides of the sheet to read 2 image signals representing the radiation image, yet another adhering and/or fading correction data acquiring method of the present invention acquiring adhering/fading correction data by scanning a stimulable phosphor sheet on which radioactive rays have been irradiated uniformly and is characterized by the fact that the shading and/or fading correction data for the front and back sides of the sheet are obtained by switching reading between the 2 photoelectric reading means while the stimulable phosphor sheet is being scanned with the stimulating rays.

The stimulable phosphor sheet is not limited to those having layers of stimulable phosphor on its front and back sides but includes those having the layer on only one side thereof.

The phrase that the radioactive rays have been irradiated uniformly means that the radioactive rays at a reference dosage have been uniformly irradiated over the entire sheet.

Switching reading by the photoelectric reading means between one side and the other side may be carried out based on the number of main scan lines having been scanned by the stimulating rays or based on time elapsed after detection of a reference signal marking the start of image signal reading.

In the case where the characteristic of shading changes in accordance with sensitivity of the photoelectric reading means such as a photomultiplier, it is preferable for each of the photoelectric reading means to change its sensitivity in addition to switching of reading by the photoelectric means so that shading correction data for different sensitivity of each photoelectric reading means can be obtained. Switching of the sensitivity of the photoelectric means may also be carried out based on the number of main scan lines having been scanned by the stimulating ray or based on the time elapsed after detection of the reference signal marking the start of the image signal reading.

The items as targets of shading correction are inequality within one line and all periodic fluctuation in each line corresponding to a polygon surface, represented by the items listed below. In other words, as items related to a light collecting system, correction of variance in light collection efficiency, light collecting guide transmission ratio and sensors can be listed. As items related to a stimulating system, variance in scanning beam strength (due to variance in reflectivity within a polygon surface and between surfaces, for example), and variance in scanning beam positioning (due to variance in position/angle of polygon surface, for example) can be listed.

According to the shading and/or fading correction data acquiring method for the radiation image reading apparatus of the present invention, shading and/or fading correction data can be obtained at the time of two-side radiation image reading, and, based on the correction data, shading and/or fading correction can be carried out on image data having been read.

Furthermore, when correction is carried out only on images of either the front or back side of stimulable phosphor sheets by applying shading correction data and/or fading correction data corresponding to the image after addition processing in order to retain uniformity of the images after addition, only one system of correction circuitry is sufficient, which is advantageous.

Moreover, when identical correction is carried out on the images on both sides of a stimulable phosphor sheet by applying shading correction and/or fading correction data corresponding to the image after addition processing, only one set of correction data is sufficient, which is also advantageous. This is especially efficient for the case where shading data (light collecting guide shape) are the same on both sides.

If the shading correction data and/or fading correction data corresponding to both sides are obtained at one time reading, it is advantageous in terms of time and cost, since the shading and/or fading correction data corresponding to the front and back sides are obtained by scanning the sheet once with stimulating rays.

In this case, if the data are stored in memories which are separated from an image memory and are for acquisition of shading correction data and/or fading correction data corresponding to both sides, necessary memory space is smaller than the image memory, since only the memories for calculation are necessary.

Likewise, in the case where the shading correction data and/or fading correction data for the front and back sides are obtained separately by 2-time reading, if the shading correction data and/or fading correction data are recorded in an image memory corresponding to only any one of the front image, the back image and the image after addition, necessary memory space is substantially smaller than the image memory, since only the memory for calculation is necessary.

Furthermore, if the plurality of shading correction and/or fading correction data sets in accordance with the reading modes such as scanning density of the stimulating rays, the beam diameter of the scanning stimulating rays, and the scanning speed are obtained and correction data corresponding to the actual reading mode among the plurality of correction data sets are used for shading correction and/or fading correction on the image signal, appropriate correction in accordance with the reading mode can be carried out.

Moreover, another shading correction and/or fading correction data acquiring method of the present invention is for a radiation image reading apparatus which scans, by using stimulating rays, a stimulable phosphor sheet on which a radiation image has been recorded and photoelectrically detects light emitted from the front and back sides of the sheet by using photoelectric reading means separately located on both sides to read 2 image signals representing the radiation image, and the shading correction data acquiring method acquires the shading correction data for both sides of the sheet by switching reading between the 2 photoelectric reading means while the stimulable phosphor sheet on which radioactive rays have been irradiated uniformly is being scanned with the stimulating rays.

According to the shading and/or fading correction data acquiring method of the present invention for the radiation image reading apparatus, by switching reading between the photoelectric reading means separately located on both sides of the sheet during the scan of the sheet with the stimulating rays, shading and/or fading correction data for the front of the sheet can be obtained during reading by the photoelectric reading means on the front side, and shading and/or fading correction data for the back side of the sheet can be obtained during reading by the photoelectric reading means on the back side. Therefore, even for a radiation image reading apparatus carrying out reading on both sides, shading and/or fading correction data for both sides can be obtained during the scan of an area equivalent to one side of the sheet, which is practical in terms of time and cost.

According to a data acquiring method wherein the shading and/or fading correction data for each side of one sheet (2 sides in total) are temporarily stored, memory space for storing data read from both sides is needed. However, according to the shading and/or fading correction data acquiring method wherein shading and/or fading correction data for both sides are obtained during scan of an area equivalent to one side, memory space for one-side data is sufficient, which leads to reduction in memory space.

DESCRIPTION OF THE PREFERRED EMBODIMENTS

Hereinafter, embodiments of a shading correction data acquiring method for a radiation image reading apparatus of the present invention will be explained with reference to the accompanying drawings.

Figure 1:
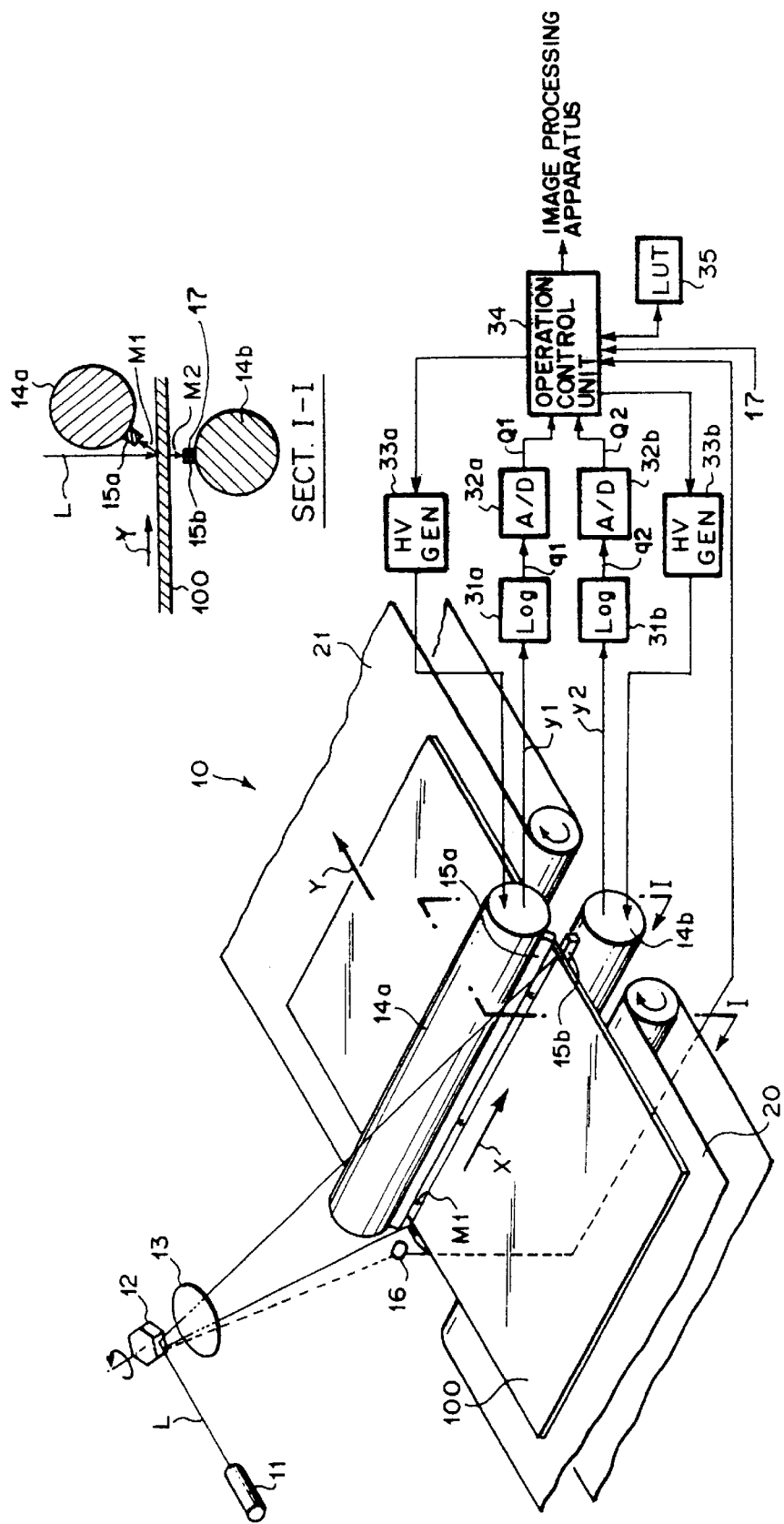
FIG. 1a is a block diagram showing a configuration of a radiation image reading apparatus to which a shading correction data acquiring method of the present invention is applied.
FIG. 1b is a cross section of the apparatus taken along the line I—I.

FIG. 1 is a block diagram showing a configuration of a radiation image reading apparatus to which the shading correction data acquiring method of the present invention is applied.

The radiation image reading apparatus shown in FIG. 1 reads radiation image information from the front and back sides of a stimulable phosphor sheet having layers of stimulable phosphor formed on the front and back thereof. The front and the back are a conventional distinction to identify one and the other sides of a sheet, and either side can be the front. In these embodiments, the front refers to the side from which radioactive rays enter upon recording of radiation image information and the back refers to the side from which the radioactive rays emerge.

In a radiation image reading apparatus 10 shown in FIG. 1, a stimulable phosphor sheet 100 (hereinafter simply called a sheet) is placed on 2 endless belts 20 and 21 which are made to revolve by a motor not shown in FIG. 1. Above the sheet 100, a laser beam source 11 which emits a laser beam L for stimulating the sheet 100, a rotational polygon mirror 12 reflecting and deflecting the laser beam L while being driven by a motor not shown in FIG. 1, and a scanning lens (fθ lens) 13 for converging the laser beam L reflected and deflected by the rotational polygon mirror 12 on the sheet 100 and for scanning the sheet at a constant speed are located. The lens 13 is a facet angle correction lens.

The sheet 100 is scanned along the main scan direction shown by an arrow X by the laser beam L while being conveyed along the direction shown by an arrow Y by the endless belts 20 and 21. Therefore, the entire surface of the sheet 100 can be scanned by the laser beam L (equivalent to 4320 lines along the main scan direction). over the front of the sheet 100 (the upper side of FIG. 1) scanned by the laser beam L, there is located a photomultiplier 14a (photomultiplier tube) which photoelectrically detects, via a light guide 15a, light M1 emitted from the front of the sheet 100 upon exposure to the laser beam L in accordance with the image information recorded on the sheet 100 and converts the light into an analog image signal y1. The photomultiplier 14a is a so-called long photomultiplier having a photodetection surface along the main scan direction of the laser beam L (the direction shown by the arrow X) to scan the front of the sheet 100. An exit end surface of the light guide 15a is connected to the photodetection surface of the photomultiplier 14a. An entrance end surface of the light guide 15a is located in proximity to the front of the sheet 100 and guides the light M1 incident from the incidence end surface to the exit end surface plane. A thin film of a stimulating ray cutting filter (not shown) is formed on the entrance end surface in order to prevent the laser beam L from entering.

A logarithmic amplifier 31a is connected to the photomultiplier 14a. The logarithmic amplifier 31a amplifies the analog image signal y1 while converting y1 into a logarithm and outputs a logarithmic image signal q1. An analog/digital conversion circuit (hereinafter called an A/D conversion circuit) 32a is connected to the logarithmic amplifier 31a. The logarithmic image signal q1 is sampled at a predetermined sampling frequency T by the A/D conversion circuit 32a and thereby converted into digital image data Q1.

On the back of the sheet 100 (the lower side of FIG. 1) scanned by the laser beam L, a light guide 15b is placed in proximity to the sheet in order to collect light M2 emitted from the back of the sheet 100 upon exposure to the laser beam L. A long photomultiplier 14b which photoelectrically detects the collected light M2 and converts the light into an analog image signal y2 is connected to the light guide 15b. A sensor 17 is buried under the light guide 15b for generating a reference signal marking the start of reading of the emitted light M2 by detecting the edge of the sheet 100 along the direction Y of conveyance by the endless belts 20 and 21 (see the cross section in FIG. 1).

A logarithmic amplifier 31b is connected to the photomultiplier 14b. The logarithmic amplifier 31b amplifies the analog image signal y2 while converting the analog image signal y2 into a logarithm and outputs a logarithmic image signal q2. An A/D conversion circuit 32b is connected to the logarithmic amplifier 31b. The logarithmic image signal q2 is sampled at the predetermined sampling frequency T by the A/D conversion circuit 32b and thereby converted into digital image data Q2 thereby.

A voltage generated by a voltage generator (HV GEN) 33a is applied to the photomultiplier 14a and a voltage generated by a voltage generator 33b is applied to the photomultiplier 14b. In accordance with these voltages, sensitivity of the photomultipliers 14a and 14b can be changed to high, semi-high, or standard. This 3-level sensitivity is only an example and 2-level sensitivity or 4 or more levels of sensitivity can also be adopted.

A starting edge detecting photodetector 16 for synchronization in a main scan direction (horizontal synchronization) is located outside the sheet 100 and at an edge of the line along which main scan by the laser beam L is carried out.

The radiation image reading apparatus 10 shown in FIG. 1 further comprises an operation control unit 34 which generates shading correction data which will be explained later by controlling timing of applying voltages to the voltage generators 33a and 33b and timing of recording the digital image data Q1 and Q2 input from the A/D conversion circuits 32a and 32b to generate a look-up table (LUT 35) from the shading correction data, and carries out shading correction referring to the LUT 35 on the digital image data Q1 and Q2 read upon a read of normal radiation image information to output the data to an image processing apparatus.

An operation of acquiring the shading correction data by using the radiation image reading apparatus 10 will be explained next.

The stimulable phosphor sheet 100 (reference sheet) on which radiation at a reference dosage has been uniformly irradiated entirely by a radiation image photographing apparatus which is not shown is set at a predetermined position on the endless belt 10. The sheet 100 placed at the predetermined position is conveyed (vertical-scanned) in the direction shown by the arrow Y by the endless belt 20.

Meanwhile, the laser beam L emitted from the laser beam is source 11 is reflected and deflected by the rotational polygon mirror 12 rotating at a high speed in the direction shown by an arrow in FIG. 1. The deflected laser beam L is converged by a scanning lens 13 on the front of the reference sheet 100 and scans the front of the reference sheet 100 horizontally in the direction of X at a constant speed. The timing of starting the main scan is detected by the starting edge detecting photodetector 16, and input to the operation control unit 34.

The sensor 17 buried under the light guide 15b on the back side of the sheet detects the laser beam L. The edge of the sheet 100 is detected by a change in intensity of the light when the sheet to be scanned vertically reaches the main scan position, and the reference signal marking the start of reading is output to the operation control unit 34 by the sensor 17.

Figure 2:
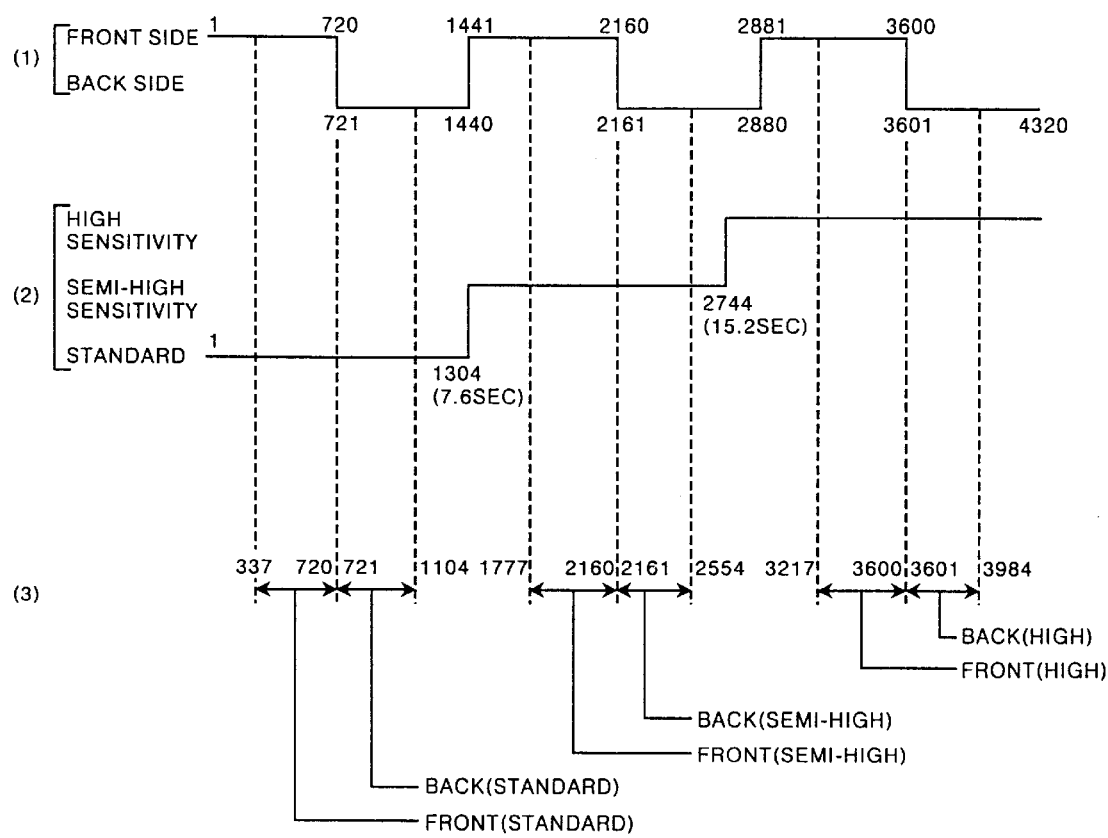
FIG. 2 is a timing chart showing timing of switching recording and sensitivity in relation to the number of main scan lines.

Based on the input reference signal marking the start of reading, the operation control unit 34 controls the voltage generators 33a and 33b so that voltages setting the sensitivity of the photomultipliers 14a and 14b to standard are applied to the photomultiplier 14a and 14b (see FIG. 2(2)). The operation control unit 34 switches internal recording circuits so that only the digital image data Q1 input from the A/D conversion circuit 32a corresponding to the front are recorded out of the digital image data Q1 and Q2 input from the A/D conversion circuits 32a and 32b respectively. Furthermore, the operation control unit 34 monitors, using a built-in timer, the time elapsed after the input of the reference signal marking the start of reading, and counts the detection signal input from the starting edge detecting photodetector 16 at every main scan which will be described later.

The monitoring of the elapsed time by the timer in the operation control unit 34 is carried out in order to specify the timing of switching sensitivity of the photomultipliers 14a and 14b. As shown in FIG. 2(2), this switching is carried out in such a manner that the sensitivity stays standard until the timer shows 7.6 sec (equivalent to the main scan lines 1to 1304), semi-high between 7.6 and 15.2 sec (equivalent to 1305 to 2744), and high after 15.2 sec.

The detection signals are counted in order to specify the timing of switching recording of the input digital image data Q1 and Q2 in accordance with the number of main scan lines. As shown in FIG. 2(1), data input from the front side are recorded from line 1 to line 720, and data input from the back side are recorded from line 721 to 1440. The data from the front side are then recorded from line 1441 to 2160, and the data from the back side are recorded from line 2161 to 2880. Thereafter, the data from the front side are recorded from line 2881 to 3600 and the data from the back side are recorded from 3601 to 4320 (the last line). In this manner, switching of recording is carried out.

The laser beam L irradiated on the reference sheet 100 stimulates the stimulable phosphor on this sheet 100, and the light M1 is emitted from the front of the sheet 100 in accordance with the radiation image information recorded thereon, while the light M2 is emitted from the back of the sheet 100 in accordance with the radiation image information recorded thereon.

The light M1 emitted from the front of the sheet 100 is lead to the photomultiplier 14a by the light guide 15a located above and in proximity to the sheet 100 and photoelectrically detected thereby. Meanwhile,the light M2 emitted from the back of the sheet 100 is lead to the photomultiplier 14b by the light guide 15b located below and in proximity to the sheet 100 and photoelectrically detected thereby. The sensitivity of the photomultipliers 14a and 14b has been set to standard by the voltages applied thereto by the voltage generators 33a and 33b respectively.

The photomultiplier 14a converts the light M1 emitted from the front of the sheet 100 and detected photoelectrically at the standard sensitivity into the analog image signal y1 and outputs the signal to the logarithmic amplifier 21a. The logarithmic amplifier 31a amplifies the analog image signal y1 in a logarithmic manner and outputs the signal as the logarithmic image signal q1 to the A/D conversion circuit 32a. The A/D conversion circuit 32a converts the input logarithmic image signal q1 to the digital image data Q1 and outputs the data to the operation control unit 34.

Meanwhile, the photomultiplier 14b converts the light M2 emitted from the back of the sheet 100 and detected at the standard sensitivity into the analog image signal y2 and outputs the signal to the logarithmic amplifier 31b. The logarithmic amplifier 31b amplifies the analog image signal y2 in a logarithmic manner and outputs the signal as the logarithmic image signal q2 to the A/D conversion circuit 32b. The A/D conversion circuit 32b converts the input logarithmic image signal q2 to the digital image data Q2 and outputs the data to the operation control unit 34.

Out of the input digital image data Q1 and Q2, the operation control unit 34 records only the digital image data Q1 input from the A/D conversion circuit 32a on the front side by using the internal recording circuit described above (see FIG. 2(1)). The same operation is repeated until the main scan line number becomes 720.

When the number of the main scan line becomes 721, the operation control unit 34 switches the internal recording circuits and records only the digital image data Q2 input from the A/D conversion circuit 32b on the back side (see FIG. 2(1)). Thereafter, the switching between the recording circuits is carried out as shown in FIG. 2(1).

While the recording circuits are switched between the front and the back sides as has been described above, the operation control unit 34 controls the voltage generators 33a and 33b at the timing shown by FIG. 2(2) described above by monitoring the built-in timer, so that the voltages applied to the photomultipliers 14a and 14b are switched. Therefore, the sensitivity of the photomultipliers 14a and 14b is sequentially switched in the order of standard, semi-high and high.

In this manner, shading correction data for each sensitivity (standard, semi-high, and high) of the photomultipliers 14a and 14b on the front and the back sides of the sheet 100 are respectively recorded in the operation control unit 34.

As has been described above, according to the shading correction data acquiring method in this embodiment, the shading correction data for both sides of the sheet 100 can be obtained for each sensitivity of the photomultipliers while the area of the sheet 100 equivalent to only one side of the sheet is being scanned with the laser beam.

Since the sensitivity of the photomultipliers becomes unstable immediately after being switched, data recorded immediately after switching are not used as shading correction data, and the shading correction data are obtained by using data recorded after a predetermined time (predetermined number of lines scanned) has elapsed, as shown in FIG. 2(3). In other words, the following data are used for calculating the shading correction data for each condition:

1) data Q1 recorded between the main scan line number 337 to 720 are data of the front side at the standard sensitivity,
2) data Q1' recorded between the main scan line number 1777 to 2160 are data of the front side at the semi-high sensitivity,
3) data Q1" recorded between the main scan line number 3217 to 3600 are data of the front side at the high sensitivity,
4) data Q2 recorded between the main scan line number 721 to 1104 are data of the back side at the standard sensitivity,
5) data Q2' recorded between the main scan line number 2161 to 2554 are data of the back side at the semi-high sensitivity, and
6) data Q2" recorded between the main scan line number 3601 to 3984 are data of the back side at the high sensitivity.

The shading correction data obtained by using the above data are set as the LUT 35. The radiation image reading apparatus 10 reads the digital image data from both sides of a stimulable phosphor sheet recording an actual radiation image, and the operation control unit 34 carries out shading correction on the digital image data read from each side by referring to the shading correction data in the LUT 35. The image data after the correction are input from the operation control unit 34 to the image processing apparatus.

When the radiation image reading apparatus 10 to which the shading correction acquiring method of the present invention is applied has a system for monitoring a fluctuation of the voltages applied to the photomultipliers for failure diagnosis, it is possible for the failure diagnosis system to misjudge the voltage switched upon acquisition of the shading correction data as an abnormality. Therefore, in the operation of acquiring the shading correction data, the diagnosis system needs to be configured to avoid such an erroneous diagnosis.

In the shading correction data acquiring method in the above embodiment, since the characteristic of shading differs depending on the sensitivity of the photomultipliers, the shading correction data are obtained for each sensitivity. However, the shading correction data acquiring method of the present invention is not limited to the above embodiment. When the characteristic of shading does not change regardless of the sensitivity, it is not necessary to obtain the shading correction data by switching the sensitivity of the photoelectric reading means (for example, photomultipliers) and only data recording needs to be switched between the front and the back. Furthermore, in the case where the sensitivity of the photoelectric reading means can vary continuously or have more levels for example, it is unnecessary to acquire the shading correction data for all sensitivity levels. In such a case, only representative shading correction data corresponding to at least 2 levels of sensitivity are obtained and shading correction data corresponding to the sensitivity used upon acquisition of actual image data can be found by interpolation processing such as linear interpolation or the like based on the obtained shading correction data at 2 (or 3 or more) levels.

Moreover, in the above embodiment, recording is switched between the front and the back (FIG. 2(1)) while the sensitivity of the photomultipliers is constant (FIG. 2(2)). However, the sensitivity may be changed during the recording for either side. In this case, since a certain time is necessary before the sensitivity of the photomultipliers becomes stable after being switched, it is preferable to switch recording between the both sides while the sensitivity is constant, as in this embodiment.

FIGS. 3 to 9 are block diagrams showing configurations of various embodiments of radiation image reading apparatuses of the present invention.

Figure 3:
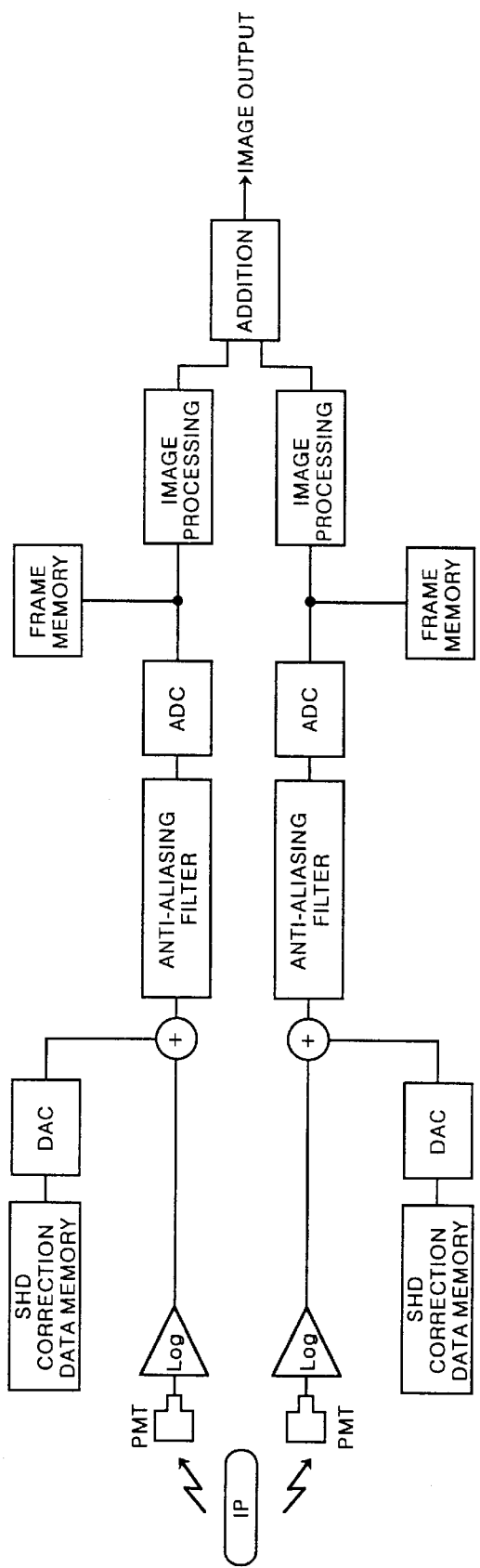
FIG. 3 is a block diagram showing another configuration of a radiation image reading apparatus to which a shading correction data acquiring method of the present invention is applied.

FIG. 3 shows an embodiment wherein shading correction data and/or fading correction data are stored in image memories respectively corresponding to each side.

Figure 4:
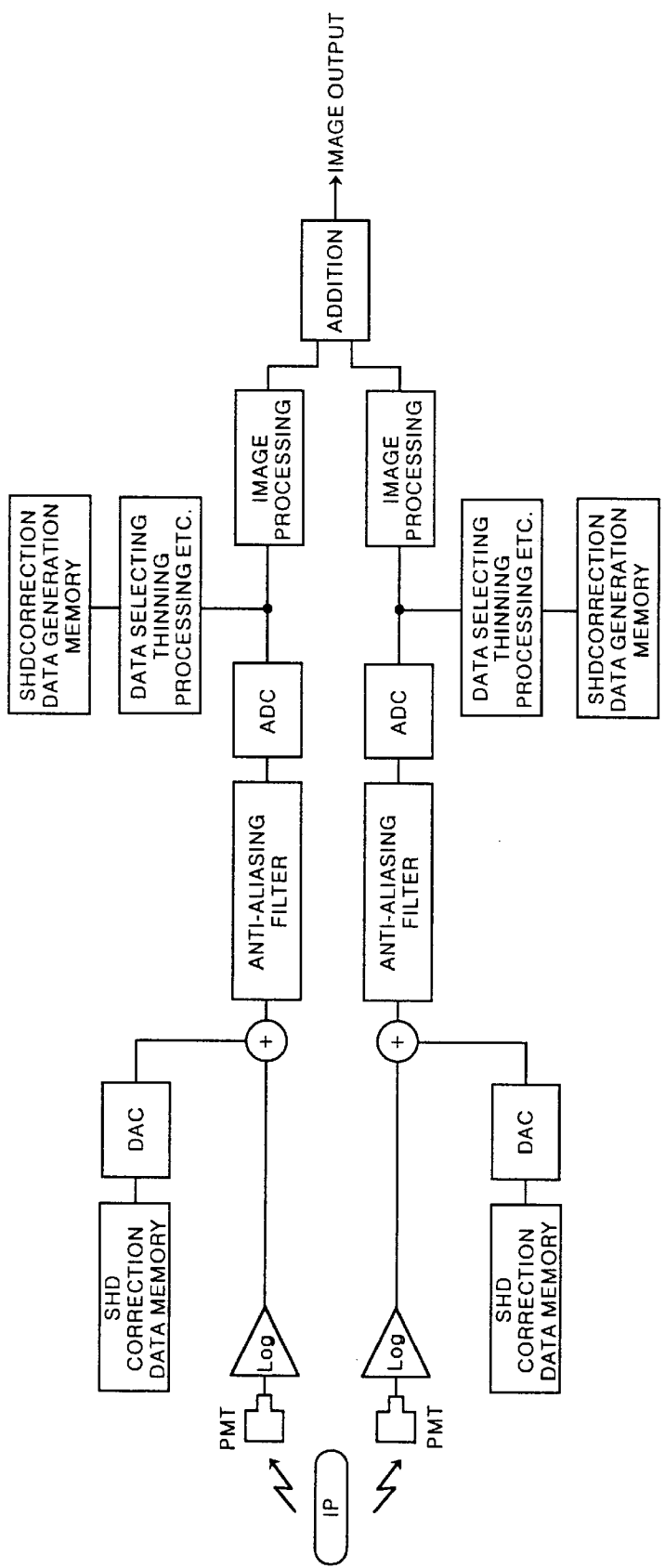
FIGS. 4 to 9 are block diagrams respectively showing another configuration of a radiation image reading apparatus to which a shading correction data acquiring method of the present invention is applied.

FIG. 4 shows an embodiment wherein shading correction data and/or fading correction data are stored in memories which are separated from an image memory and are for acquisition of shading correction data and/or fading correction data corresponding to each side.

Figure 5:
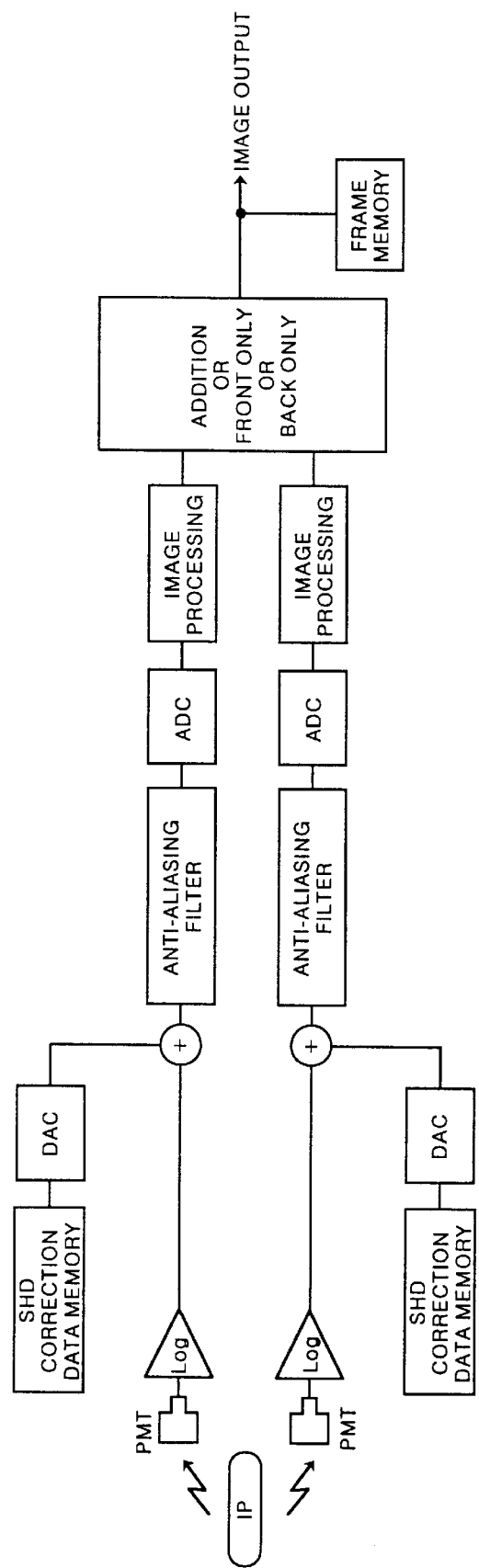

FIG. 5 shows an embodiment wherein shading correction data and/or fading correction data are stored in an image memory corresponding to only any one of the front side image, the back side image, or the image after addition processing.

Figure 6:
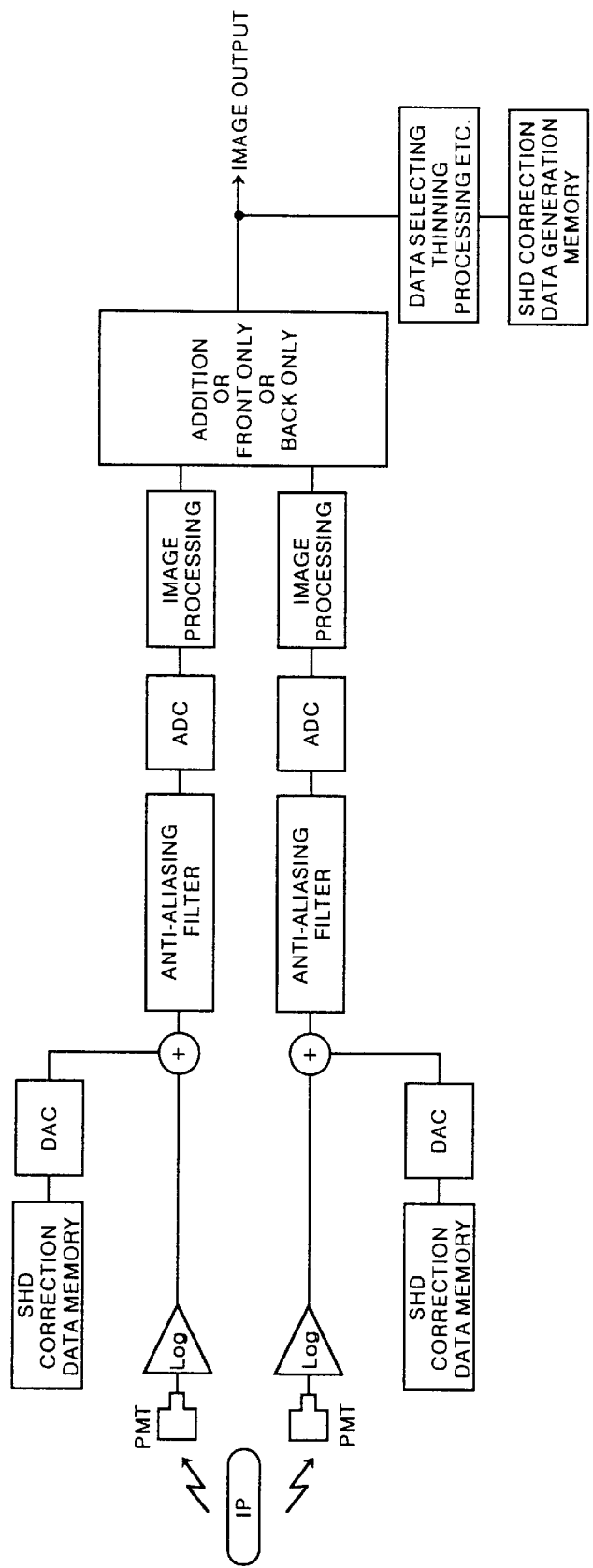

FIG. 6 shows an embodiment wherein shading correction data and/or fading correction data are stored in a memory which is separated from an image memory and is for acquisition of shading correction data and/or fading correction data corresponding to only any one of the front side image, the back side image, or the image after addition processing.

Figure 7:
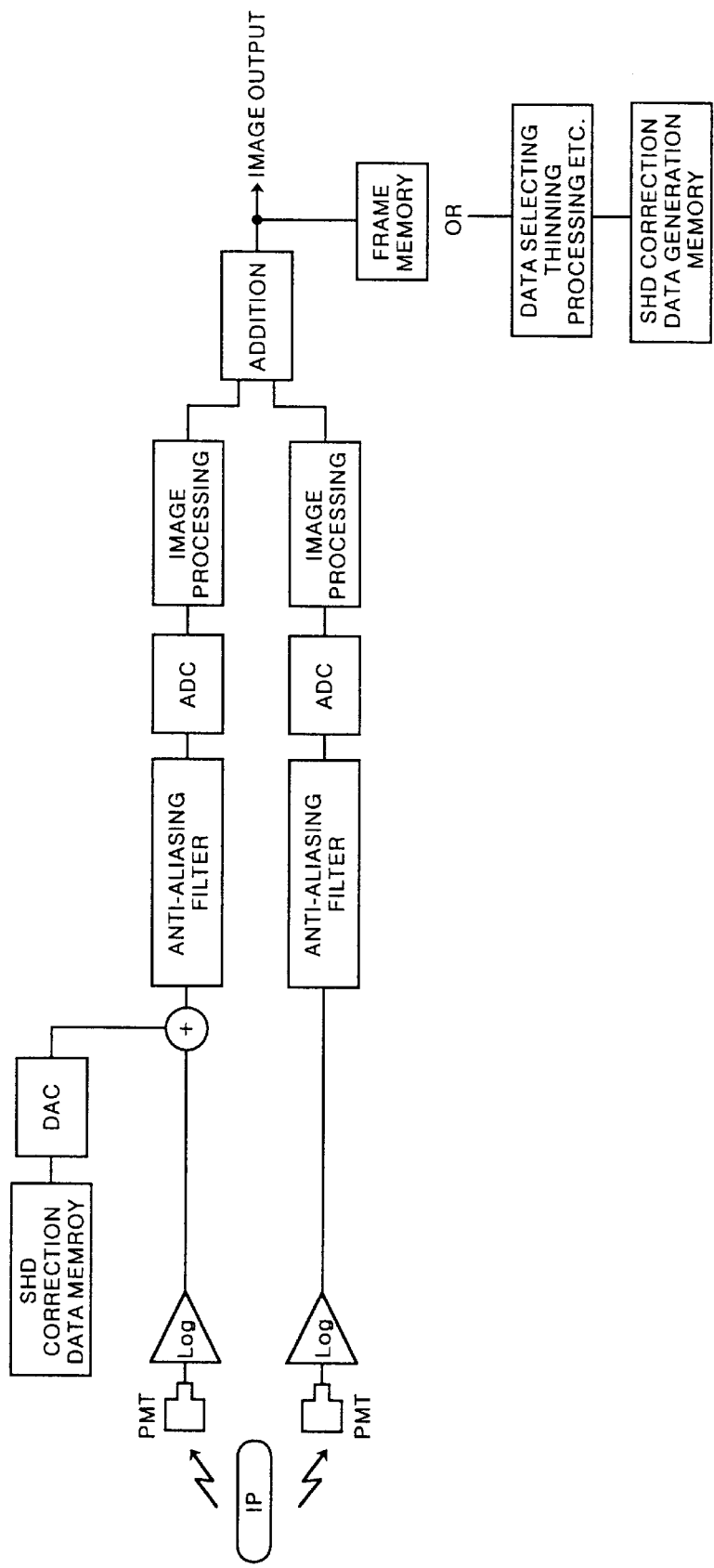

FIG. 7 shows an embodiment wherein correction is carried out on images corresponding to only the front side or the back side of a stimulable phosphor sheet by using shading correction data and/or fading correction data corresponding to an image after addition processing so that uniformity of images after addition processing can be retained.

Figure 8:
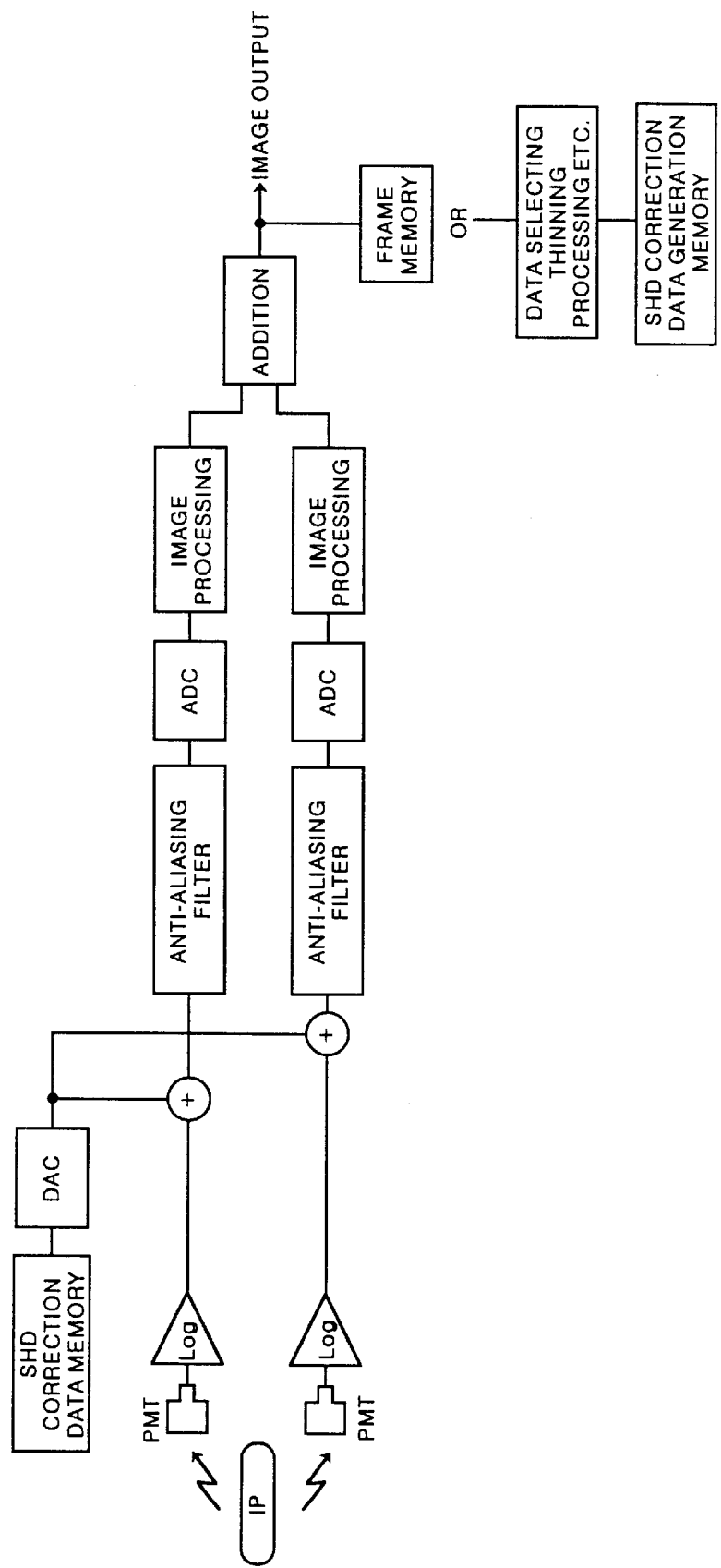

FIG. 8 shows an embodiment wherein identical correction is carried out on images corresponding to the front and back sides of a stimulable phosphor sheet by using shading correction data and/or fading correction data corresponding to an image after addition processing so that uniformity of images after addition processing can be retained.

Figure 9:
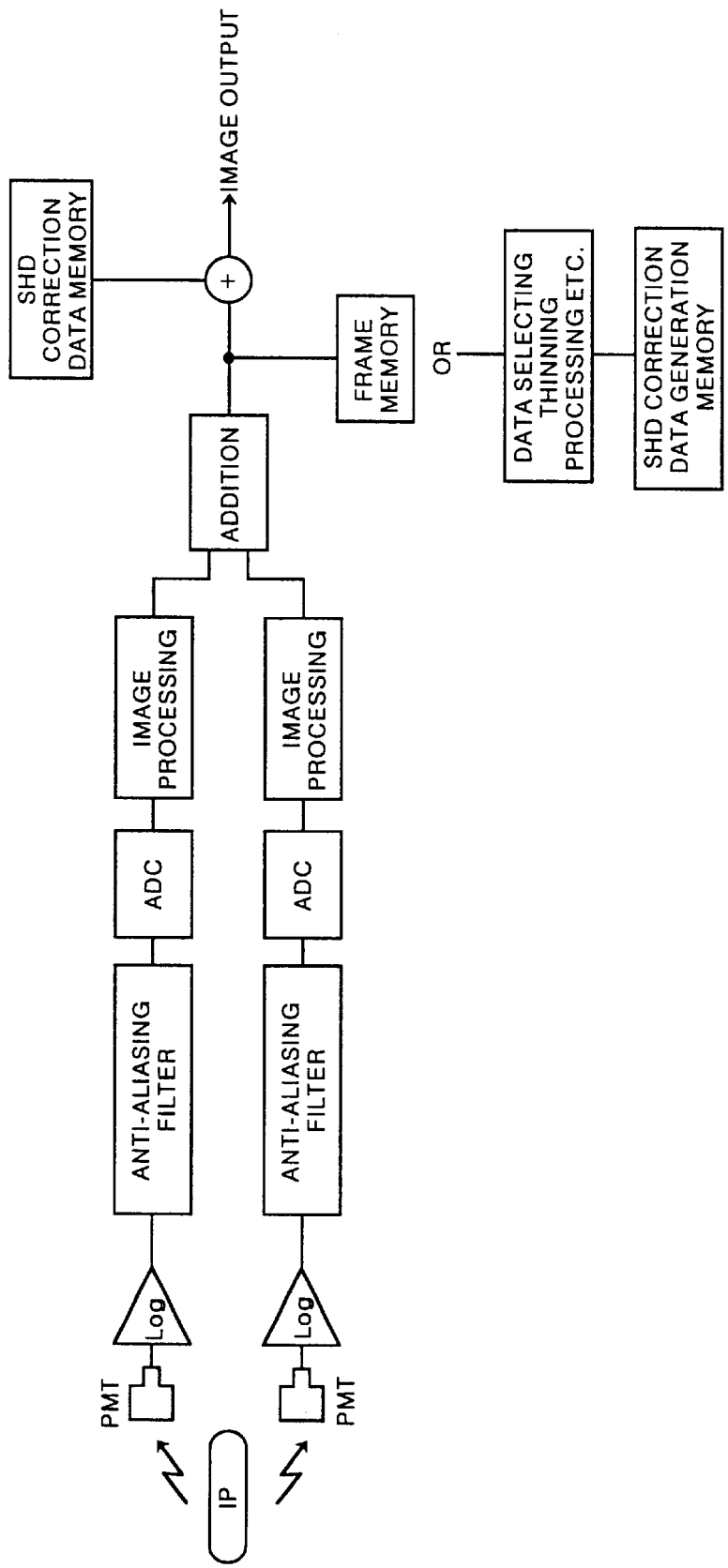

FIG. 9 shows an embodiment wherein correction is carried out on images after addition by using shading correction data and/or fading correction data corresponding to an image after addition processing.

As an algorithm for generating the shading correction data, algorithms listed below can be adopted. In the algorithms below, each line corresponding to a polygon surface is averaged (added) and high frequency components are eliminated by carrying out filtering processing (masking operation in the explanation below).

In this algorithm example, data are held as shading at a reference polygon surface (shading correction data) and values (polygon correction data) for each polygon surface relative to the reference surface (5 surfaces excluding the reference surface), which enables changing only the shading correction data or only the polygon correction data. (The shading correction data in the above embodiment refers to both the shading correction data and the polygon correction data here).

1) Acquisition of data for correction calculation

An image having uniform exposure is read and data for calculation are stored in an image memory (or in shading correction calculation memory).

2) Addition processing for each polygon surface Image data of each pixel are added at every so many polygon surfaces (in this example, at every 6 lines, since the number of polygon surfaces is 6) over a range staring from the calculation start line to the lines to be averaged (384 in this example). As a result, data of 6 surfaces added for 64 lines are obtained. (The calculation start line is always set at the reference polygon surface).

3) Smoothing along the main direction 3.1 Processing for both ends

Shading correction data immediately after recording may include unnecessary data which are for range out of the stimulable phosphor sheet. Therefore, that portion is cut by a predetermined width and processing such as embedding Of neighboring image data is carried out.

3.2 Smoothing by moving average

Moving average by mask size M is carried out. In order to match the number of pixels after smoothing, the processing is carried out after image data for starting point and ending point are extended by (M−1)/2 pixels.

Moving average means the processing below.

1: A first M data are averaged and the result is used as first data.

2: The subsequent M data are averaged and the result is used as second data.

N+α: M data from (N+α)th data are averaged and the result is used as (N+α)th data.

The above processing is carried out for all polygon surfaces (6 surfaces).

4) If necessary, thinning is carried out in the main direction.

5) An average of the table is found and correction data are drawn.

5.1 An average Qc of the table is found.

$$Qc = \Sigma Qij/(6 \times (N+\alpha)/8)$$

5.2 For data Q1j of the first surface table, a difference from Qc is found and SHD correction data Sj are found.

5.3 Polygon data are calculated

Polygon data $Pij = Q1j - Qij$ (i=2~6)

In actual correction, from
shading data Si and
polygon data Pij, shading/polygon correction data SPij is found by using the equations below to obtain a correction table:

sp1j=Sj

SPij=Sj+Pij (i=2~6).

Figure 10:
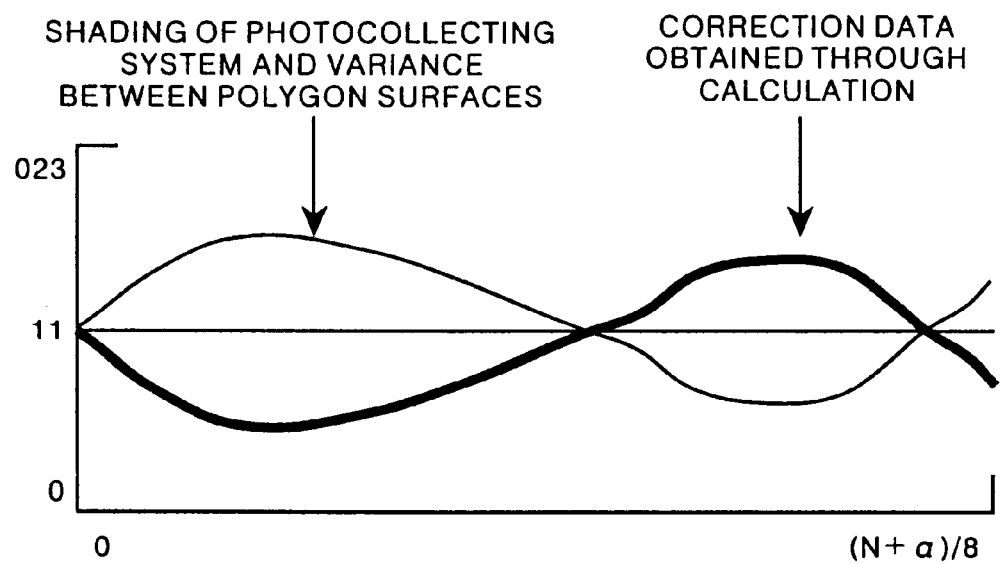
FIG. 10 is a graph showing an example of acquiring shading correction data through calculation using an example of the shading correction data acquiring method of the present invention.

The shading/polygon correction data obtained through the above calculation can be represented by the graph in FIG. 10. By adding the data to the image signal using hardware, shading of a light collecting system and variance between polygon surfaces can be canceled.

What is claimed is:

1. A two-side radiation image reading method comprising the steps of scanning a stimulable phosphor sheet having a radiation image recorded thereon, photoelectrically detecting light emitted from the front and back sides of the sheet by using photoelectric reading means separately located on the front and back sides of the sheet to read two image signals representing the radiation image, and obtaining a final image by carrying out addition processing on the two image signals, the radiation image reading method further including the steps of acquiring shading correction and/or fading correction data in advance and carrying out shading correction and/or fading correction on the image signals by using the shading correction and/or fading correction data having been obtained, wherein correction is carried out for images only on the front side or the back side of stimulable phosphor sheets by applying shading correction and/or fading correction data for the image after addition processing so that uniformity of the images after addition can be retained.

2. A two-side radiation image reading method comprising the steps of scanning a stimulable phosphor sheet having a radiation image recorded thereon, photoelectrically detecting light emitted from the front and back sides of the sheet by using photoelectric reading means separately located on the front and back sides of the sheet to read two image signals representing the radiation image, and obtaining a final image by carrying out addition processing on the two image signals, the radiation image reading method further including the steps of acquiring shading correction and/or fading correction data in advance and carrying out shading correction and/or fading correction on the image signals by using the shading correction and/or fading correction data having been obtained, wherein identical correction is carried out for images on the front and back sides of a stimulable phosphor sheet by applying shading correction and/or fading correction data for the image after addition processing so that uniformity of images after addition can be retained.

3. A two-side radiation image reading method comprising the steps of scanning a stimulable phosphor sheet having a radiation image recorded thereon, photoelectrically detecting light emitted from the front and back sides of the sheet by using photoelectric reading means separately located on the front and back sides of the sheet to read two image signals representing the radiation image, and obtaining a final image by carrying out addition processing on the two image signals, the radiation image reading method further including the steps of acquiring shading correction and/or fading correction data in advance and carrying out shading correction and/or fading correction on the image signals by using the shading correction and/or fading correction data having been obtained, wherein correction is carried out on images after addition by applying shading correction and/or fading correction data for the image after addition processing.

4. A correction data acquiring method used in a radiation image reading method wherein a stimulable phosphor sheet having a radiation image recorded thereon is scanned with stimulating rays and light emitted from the sheet is photoelectrically detected by using photoelectric reading means to obtain an image signal representing the radiation image, the correction data acquiring method being characterized by the fact that a plurality of shading correction and/or fading correction data sets corresponding to reading modes comprising at least one of: a scanning density of the stimulating rays, a beam diameter of the scanning stimulating rays, and a scanning speed are obtained.

5. A radiation image reading method comprising the steps of scanning a stimulable phosphor sheet having a radiation image recorded thereon with stimulating rays, and photoelectrically detecting light emitted from the sheet by using photoelectric reading means to obtain an image signal representing the radiation image, the method further including the steps of obtaining in advance a plurality of shading correction and/or fading correction data sets corresponding to reading modes comprising at least one of: scanning density of the stimulating rays, a beam diameter of the scanning stimulating rays, and a scanning speed, and carrying out correction on the image signal by using a shading correction data and/or fading correction data set corresponding to an actual reading mode among the plurality of shading correction and/or fading correction data sets.

6. A two-side radiation image reading apparatus which scans, with stimulating rays, a stimulable phosphor sheet having a radiation image recorded thereon, photoelectrically detects light emitted from the front and back sides of the sheet by using photoelectric reading means separately located on both sides of the sheet to read two image signals representing the radiation image, and obtains a final image by carrying out addition processing on the two image signals, the radiation image reading apparatus comprising:

correction means for carrying out shading correction and/or fading correction on the image signals by using shading correction and/or fading correction data having been obtained in advance, wherein the correction means carries out correction on images of only the front side or back side of stimulable phosphor sheets by applying shading correction data and/or fading correction data for the image after addition processing so that uniformity of the images after addition can be retained.

7. A two-side radiation image reading apparatus which scans, with stimulating rays, a stimulable phosphor sheet having a radiation image recorded thereon, photoelectrically detects light emitted from the front and back sides of the sheet by using photoelectric reading means separately located on both sides of the sheet to read two image signals representing the radiation image, and obtains a final image by carrying out addition processing on the two image signals, the radiation image reading apparatus comprising:

correction means for carrying out shading correction and/or fading correction on the image signals by using shading correction and/or fading correction data having been obtained in advance, wherein the correction means carries out identical correction on images of the front and back sides of a stimulable phosphor sheet by applying shading correction and/or fading correction data for the image after addition processing so that uniformity of images after addition can be retained.

8. A two-side radiation image reading apparatus which scans, with stimulating rays, a stimulable phosphor sheet having a radiation image recorded thereon, photoelectrically detects light emitted from the front and back sides of the sheet by using photoelectric reading means separately located on both sides of the sheet to read two image signals representing the radiation image, and obtains a final image by carrying out addition processing on the two image signals, the radiation image reading apparatus comprising:

correction means for carrying out shading correction and/or fading correction on the image signals by using shading correction and/or fading correction data having been obtained in advance, wherein the correction means carries out correction on an image after addition by applying shading correction and/or fading correction data for the image after addition processing.

9. A shading correction data and/or fading correction data acquiring method for a two-side radiation image reading apparatus which scans, with stimulating rays, a stimulable phosphor sheet having a radiation image recorded thereon and photoelectrically detects light emitted from the front and back sides of the sheet by using photoelectric reading means separately located on both sides of the sheet to read two image signals representing the radiation image, the method being characterized by the fact that shading correction data and/or fading correction data corresponding to the front and back sides are obtained at one-time reading.

10. A correction data acquiring method as claimed in claim 9, wherein the shading correction data and/or fading correction data are stored in image memories corresponding to the front and back sides.

11. A correction data acquiring method as claimed in claim 9, wherein the shading correction data and/or fading correction data are stored in memories which are separated from an image memory and are for acquisition of shading correction data and/or fading correction data corresponding to the front and back sides.

12. A shading correction data and/or fading correction data acquiring method for a two-side radiation image reading apparatus which scans, with stimulating rays, a stimulable phosphor sheet having a radiation image recorded thereon and photoelectrically detects light emitted from the front and back sides of the sheet by sing photoelectric reading means separately located on both sides of the sheet to read two image signals representing the radiation image, the method being characterized by the fact that shading correction data and/or fading correction data corresponding to the front and back sides are obtained at two-time reading each of which is for the front side and back side respectively.

13. A correction data acquiring method as claimed in claim 12, wherein the shading correction data and/or fading correction data are stored in an image memory corresponding to only any one of the front side image, the back side image, or an image after addition.

14. A correction data acquiring method as claimed in claim 13, wherein the shading correction data and/or fading correction data are stored in a memory which is separated from an image memory and is for acquisition of shading correction data and/or fading correction data corresponding to only any one of the front side image, the back side image, or an image after addition.

15. A shading correction data and/or fading correction data acquiring method for a two-side radiation image reading apparatus which scans, with stimulating rays a stimulable phosphor sheet having a radiation image recorded thereon and photoelectrically detects light emitted from the front and back sides of the sheet by using photoelectric reading means separately located on both sides of the sheet to read two image signals representing the radiation image, the method being characterized by the fact that shading correction data and/or fading correction data are obtained through calculation using an image after addition.

16. A shading correction data and/or fading correction data acquiring method for a two-side radiation image reading apparatus which scans, with stimulating rays, a stimulable phosphor sheet having a radiation image recorded thereon and photoelectrically detects light emitted from the front and back sides of the sheet by using photoelectric reading mans separately located on both sides of the sheet to read two image signals representing the radiation image, the method being characterized by the fact that a plurality of shading correction and/or fading correction data sets corresponding to reading modes comprising at least one of: a scanning density of the stimulating rays, a beam diameter of the scanning stimulating rays, and a scanning speed are obtained.

17. A correction data acquiring method used in a two-side radiation image reading method comprising the steps of scanning, with stimulating rays, a stimulable phosphor sheet having radiation image recorded thereon, photoelectrically detecting light emitted from the front and back sides of the sheet by using photoelectric reading means separately located on both sides of the sheet to read two image signals representing the radiation image, and obtaining a final image by carrying out addition processing on the two image signals, the correction data acquiring method being characterized by the fact that a plurality of shading correction and/or fading correction data sets corresponding to reading modes comprising at least one of: a scanning density of the stimulating rays, a beam diameter of the scanning stimulating rays, and a scanning speed are obtained.

18. A shading correction data and/or fading correction data acquiring method for a radiation image reading apparatus which scans, with stimulating rays, a stimulable phosphor sheet having a radiation image recorded thereon and photoelectrically detects light emitted from the front and back sides of the sheet by using photoelectric reading means located separately on both sides of the sheet to read two image signals representing the radiation image, the method including the step of acquiring shading correction data and/or fading correction data by scanning, with the stimulating rays, a stimulable phosphor sheet that has been irradiated uniformly with radiation, and being characterized by the fact that the shading correction data and/or fading correction data corresponding to the front and back sides of the sheet are obtained by switching reading between the two photoelectric reading means while the sheet is being scanned with the stimulating rays.

19. A shading correction data and/or fading correction data acquiring method as claimed in claim 18, wherein switching of the two photoelectric reading means is carried out based on the number of main scan lines having been scanned with the stimulating rays or based on time elapsed after detection of a reference signal marking the start of image signal reading.

20. A shading correction data and/or fading correction data acquiring method as claimed in claim 18, wherein switching of sensitivity of the two photoelectric reading means is carried out so that shading correction and/or fading correction data sets corresponding to a plurality of sensitivity levels of the photoelectric reading means are obtained.

21. A shading correction data and/or fading correction data acquiring method as claimed in claim 20, wherein switching of sensitivity of the two photoelectric reading means is carried out based on the number of main scan lines having been scanned with the stimulating ray or based on time elapsed after detection of a reference signal marking the start of image signal reading.

* * * * *